(12) United States Patent
Van Der Kelen et al.

(10) Patent No.: US 12,330,096 B2
(45) Date of Patent: Jun. 17, 2025

(54) PROCESS FOR SEPARATING MOLECULES FROM A MIXTURE OF FLUIDS COMPRISING AT LEAST ONE FLUORINATED COMPONENT

(71) Applicant: DEHON SAS, Paris (FR)

(72) Inventors: Patrick Van Der Kelen, Sint-Niklaas (BE); Christophe Dehon, Bry sur Marne (FR); Chien Bin Soo, Kaohsiung (TW)

(73) Assignee: DEHON SAS, Paris (FR)

( * ) Notice: Subject to any disclaimer, the term of this patent is extended or adjusted under 35 U.S.C. 154(b) by 212 days.

(21) Appl. No.: 18/030,939

(22) PCT Filed: Sep. 28, 2021

(86) PCT No.: PCT/EP2021/076716
§ 371 (c)(1),
(2) Date: Apr. 7, 2023

(87) PCT Pub. No.: WO2022/078755
PCT Pub. Date: Apr. 21, 2022

(65) Prior Publication Data
US 2023/0415066 A1   Dec. 28, 2023

(30) Foreign Application Priority Data
Oct. 12, 2020   (FR) ...................... 2010422

(51) Int. Cl.
*B01D 3/36*   (2006.01)
*B01D 3/40*   (2006.01)
(Continued)

(52) U.S. Cl.
CPC .............. *B01D 3/36* (2013.01); *B01D 3/40* (2013.01); *B01D 3/42* (2013.01); *B01D 3/4294* (2013.01); *C07C 17/386* (2013.01)

(58) Field of Classification Search
CPC .......... B01D 3/36; B01D 3/4294; B01D 3/40; B01D 3/42; B01D 3/4211; C07C 17/386
See application file for complete search history.

(56) References Cited

U.S. PATENT DOCUMENTS 6,047,560 A    4/2000  Nishimura et al.
7,371,309 B2   5/2008  Boehmer et al.

FOREIGN PATENT DOCUMENTS

WO       9703936 A1    2/1997
WO    2007038363 A2    4/2007

OTHER PUBLICATIONS

ISA European Patent Office, International Search Report Issued in Application No. PCT/EP2021/076716, Dec. 22, 2021, WIPO, 6 pages.

*Primary Examiner* — Renee Robinson
(74) *Attorney, Agent, or Firm* — Alleman Hall & Tuttle LLP

(57) ABSTRACT

Disclosed is a method for separating a plurality of chemical components from a chemical mixture comprising a plurality of fluorinated fluids, the method comprising: • a step of identifying, in the chemical mixture, at least two sub-mixtures, each complex sub-mixture being associated either with a first group for secondary pressure swing distillation or with a second group (G2) for secondary extractive distillation, • a step of primary distillation, using a main column, so as to separate each identified sub-mixture, • a secondary distillation step, using the same advanced unit of two auxiliary columns, for distilling each complex sub-mixture, the complex sub-mixtures of the first group being separated by the pressure swing distillation method and the complex sub-mixtures of the second group being separated by the extractive distillation method.

10 Claims, 3 Drawing Sheets

(51) Int. Cl.
*B01D 3/42* (2006.01)
*C07C 17/386* (2006.01)

PROCESS FOR SEPARATING MOLECULES FROM A MIXTURE OF FLUIDS COMPRISING AT LEAST ONE FLUORINATED COMPONENT

The present invention relates to the field of fluorinated fluids and more particularly aims at a process for separating by distillation the molecules present in a mixture of fluids comprising at least one fluorinated fluid.

In a known manner, a fluorinated fluid is a fluid that allows the implementation of a thermodynamic cycle in a cold production device (such as a cold room, a freezer for example) or in a hot production device (such as a heat pump for example), acting as an aerosol propellant, extinguishing agent or expansion agent. The fluorinated fluid commonly comprises a pure chemical component, or pure molecule, or a mixture of chemical components.

Such chemical components are known as HydroFluoroCarbon (HFC), consisting of hydrogen, fluorine and carbon atoms, HydroFluoroOlefin (HFO) and/or HydroChloroFluoroOlefin (HCFO) molecules. Among HFC/HFO/HCFO components are mainly known R-1234yf/ze, R-134a, R-32 used for refrigeration, air conditioning and heat pumps, R-227ea used in fire suppression systems, R-125, R-152a and R-143a used in mixtures with other components. Also, a fluorinated fluid designates any fluid comprising at least one fluorine molecule. As such, in this document, a fluorinated fluid may or may not comprise a hydrocarbon molecule.

In a known manner, at the end of their service life fluorinated refrigerants comprise pollutants and have to be recovered. For example, during an operation of maintenance or dismantling of thermodynamic systems, the device is purged in order to recover the used fluorinated fluid. This must then be treated to remove the impurities. Further, for a mixture of chemical components, each component of the mixture must be isolated in order to be brought back into line with standards and thus allow its reuse.

In a known manner, in a used fluorinated fluid, the different chemical components are separated by a simple column distillation method, known to those skilled in the art. In such a distillation, an initial mixture of several components is placed in a liquid state in a tank forming a first column. In a known manner, a component is in vapor phase above its boiling temperature at a given pressure. Since each fluid has a different composition in gas and liquid phase, in the case of zeotropic mixtures, it is possible to separate the components by a simple distillation process.

However, for azeotropic or pseudo-azeotropic mixtures, i.e. comprising several components having identical or almost identical compositions in gas phase and in liquid phase for a specific composition, such a simple separation is not possible. This is also the case for so-called "tight" mixtures, i.e. mixtures comprising several components having identical or almost identical compositions in gas phase and in liquid phase on an area of the compositions.

To separate the components of an azeotropic mixture, two advanced distillation processes are known either by pressure swing or by extraction using an entraining agent, known as a solvent. In a pressure swing distillation, the fluid evolves successively, in continuous circuit in two columns set at different pressures. The function of each column is to separate one of the fluid components according to the pressure at which it is set.

In an extraction distillation, a solvent is added to the mixture of fluorinated fluids, so as to create a physical reaction between the solvent and one of the components of the azeotropic or tight fluid. The reaction then makes it possible to isolate one of the components having interacted with the solvent. The component having interacted with the solvent is then separated from the other components by simple distillation.

Many documents such as the patent applications U.S. Pat. No. 7,371,309, WO2007038363 or WO9703936 describe the separation of components from an azeotropic mixture using the aforementioned distillation methods. However, each prior art targets a particular mixture and describes a specific method or solvents to separate two or three specific components. Such an approach has a significant drawback, because it requires the treatment of each fluorinated fluid independently. Such a case-by-case treatment is time consuming and impractical because it requires the separation process to be adapted to each fluid and does not allow an overall treatment of a mixture of several fluorinated fluids comprising different components.

Furthermore, hydrofluorocarbon HFC molecules have an impact on the greenhouse effect. Also, the latter are now increasingly being replaced by more environmentally friendly hydrofluoroolefin (HFO) or hydrochlorofluoroolefin (HCFO) molecules. With regard to such molecules, the prior art also targets the distillation of particular molecules each time. Consequently, there is currently no effective method enabling the separation of all HFO or HCFO molecules.

The invention thus aims to eliminate at least some of these drawbacks by proposing a fast and reliable method for separating the components of a mixture of fluorinated fluids making it possible to separate the chemical components of an azeotropic mixture regardless of the hydrofluorocarbon or hydrofluoroolefin molecules that compose it. The method according to the invention further aims to separate the chemical components of a mixture of several fluorinated fluids of different compositions and which may contain hydrocarbons.

SUMMARY

The invention relates to a method for separating a plurality of chemical components from a chemical mixture, the chemical mixture comprising a plurality of fluorinated fluids, each fluorinated fluid comprising at least one fluorinated chemical component, the method comprising:
- a step of identification in the chemical mixture of at least two sub-mixtures, each sub-mixture being a simple sub-mixture comprising a single chemical component or a complex sub-mixture comprising a combination of chemical components, each complex sub-mixture being associated either with a first secondary distillation group by a pressure swing distillation method or with a second secondary distillation group by an extraction distillation method,
- a primary distillation step, by means of a simple main distillation column, so as to separate each identified sub-mixture,
- a secondary distillation step, by means of the same advanced unit of two auxiliary extraction columns, of each complex sub-mixture of the first group and of the second group, the complex sub-mixtures of the first group being separated by the pressure swing distillation method and the complex sub-mixtures of the second group being separated, by means of the same solvent, by the extraction distillation method, by the same two auxiliary columns.

Such a separation process advantageously enables the overall treatment of a plurality of fluorinated fluids of different types and coming from different locations. Consequently, thanks to the invention, it is no longer necessary to treat each fluorinated fluid independently, which allows a simple and fast separation of all the components of the mixture of fluorinated fluids that may contain hydrocarbons.

Advantageously, the same unit of two auxiliary columns allows both pressure swing distillation and extraction distillation to be implemented, which makes it possible to limit the number of auxiliary columns, which represents a significant cost limitation.

Consequently, the separation process according to the invention makes it possible to efficiently separate the chemical components of a complex sub-mixture irrespective of the advanced distillation method adapted to separate its chemical components.

The separation process according to the invention further advantageously makes it possible to treat a plurality of complex sub-mixtures by an extraction distillation method using a single solvent. Consequently, thanks to the invention, it is not necessary to adapt the solvent to the chemical components present in each sub-mixture. The single solvent allows chemical components to be separated from a complex sub-mixture regardless of the chemical molecules that compose it.

Thanks to the step of prior identification of each sub-mixture and association of each with a group with a view to a specific advanced distillation, the process according to the invention makes it possible to classify each sub-mixture even before the first distillation. In this way, it is possible, thanks to the invention, to proceed with the secondary distillation step for complex sub-mixtures directly after the primary distillation step, which represents a significant time saving.

Preferably, each complex sub-mixture is azeotropic or tight. Consequently, thanks to the invention, it is no longer necessary to adapt the separation process to the chemical components, as was the case in the prior art.

Preferably, the solvent is selected from the following solvents: n-pentane, dichloromethane, methyl isobutyl ketone (MIBK), methyl ethyl ketone (MEK), heptanone, pentanone, cyclohexanone and dimethylether. Preferably, the compound used is methyl isobutyl ketone (MIBK). Such a solvent advantageously makes it possible to benefit from a high separation factor and a high extraction capacity for advanced distillation and recovery of the chemical component.

Preferably, at least one of the chemical components of at least one sub-mixture is a hydrofluoroolefin HFO, a hydrochlorofluoroolefin HCFO or a hydrofluorocarbon HFC. Consequently, thanks to the invention, it is possible to separate hydrofluoroolefin HFO/HCFO components reliably and quickly. The separation process according to the invention makes it possible to separate all the chemical components from the chemical mixture regardless of their nature. Consequently, even hydrofluoroolefin HFO/HCFO components can be reused individually, unlike separation methods of the prior art that did not allow the separation of sub-mixtures of hydrofluoroolefin HFO/HCFO components in an efficient manner.

Preferably, each sub-mixture comprises one or more of the following chemical components: R-134a, R-125, R-32, R227ca, R-143a, R22 R-1234yf, R1234ze, R1233zd.

Preferably, the identification step is performed from a database associating sub-mixtures with a secondary pressure swing distillation method or a secondary extraction distillation method. Such a database allows rapid identification of the appropriate advanced distillation method for each sub-mixture of chemical components. Further, after primary distillation, the advanced distillation methods used are advantageously separation methods which are simple to implement.

Preferably, several secondary distillation steps are carried out successively for each complex sub-mixture of the first group and of the second group.

Preferably, the process comprises a preliminary step of collecting a plurality of fluorinated fluids comprising different chemical components and mixing several fluorinated fluids among the collected fluorinated fluids, so as to form at least one chemical mixture of fluorinated fluids. The process according to the invention thus enables the treatment of several chemical mixtures resulting from a plurality of fluorinated fluids of different types and collected at different locations. Consequently, it is no longer necessary to distill each fluorinated fluid independently.

Preferably, the process comprises, after the preliminary collection step, a step of analyzing each fluorinated fluid, detecting a plurality of chemical components in each fluorinated fluid, and classifying the plurality of fluorinated fluids into a plurality of predetermined mixtures according to the chemical components detected.

The invention also targets a method for recycling the chemical components of a mixture of fluorinated fluids comprising the steps of the separation process as described previously and a step of independent recycling of each chemical component.

Finally, the invention relates to a separation system for implementing the process as described previously, the separation system comprising:
- a simple main distillation column configured to receive the chemical mixture of fluorinated fluids and to implement a primary distillation, so as to separate the chemical mixture into at least two sub-mixtures,
- an electronic calculator configured to:
  - identify in the chemical mixture the different sub-mixtures, each sub-mixture being a simple sub-mixture comprising a single chemical component or a complex sub-mixture comprising a combination of chemical components,
  - associate each complex sub-mixture either with a first secondary distillation group by a pressure swing method or with a second secondary distillation group by an extraction distillation method,
- an advanced unit comprising two auxiliary extraction columns, configured to implement a secondary distillation and to allow both an extraction distillation by means of an entrainer and a pressure swing distillation, so as to separate all the chemical components of each sub-mixture.

Preferably, the system comprises only a single simple main distillation column and preferably only a single advanced unit comprising two auxiliary extraction columns. The system has a minimalist design in which the advanced unit has several uses.

The system according to the invention advantageously makes it possible to receive a mixture of fluorinated fluids and to separate each chemical component from the chemical mixture individually. The system further enables the identification of several sub-mixtures before any primary distillation making it possible to separate each sub-mixture. The separation system allows the separation of any chemical component even if the latter is included in an azeotropic sub-mixture.

Advantageously, the separation system makes it possible, by means of two auxiliary columns, to implement an advanced distillation by pressure swing or an advanced distillation by extraction according to the sub-mixture that the two auxiliary columns receive.

Preferably, the advanced unit consists of two auxiliary columns, configured to allow the implementation either of an advanced distillation by extraction or an advanced distillation by pressure swing. The separation system therefore only comprises three distillation columns (one main column and two auxiliary columns), which saves space and is very economical.

Preferably, the separation system comprises a solvent tank configured to supply one of the two auxiliary columns when the latter receives a complex sub-mixture of the second group.

DESCRIPTION OF THE DRAWINGS

The invention will be better understood upon reading the following description, given solely as an example, and by referring to the accompanying figures, given as non-limiting examples, wherein identical references are given to similar objects and wherein.

It should be noted that the figures set out the invention in detail in order to implement the invention, said figures can of course be used to better define the invention if necessary.

DETAILED DESCRIPTION

The invention relates to a process for separating a plurality of chemical components C1, C21, C22, C3, C41, C42, C51, C52 from a chemical mixture M1-M4. The chemical mixture M1-M4 comprises a plurality of fluorinated fluids F1-F6. In this example, each fluorinated fluid F1-F6 comprises at least one fluorinated chemical component and may or may not comprise one or more hydrocarbons. Subsequently, for the sake of brevity, all the chemical components C1, C21, C22, C3, C41, C42, C51, C52 will be designated by the notation Cx.

Preferably, the different fluorinated fluids F1-F6 may be of a similar or different nature and have been previously used to enable the implementation of a thermodynamic cycle in a plurality of independent thermodynamic devices. A thermodynamic device is understood to mean a cold production device (such as a cold room, a freezer or a refrigerator), a hot production device (such as a heat pump), or an aerosol dispenser, for example.

With reference to [FIG. 1], all the fluorinated refrigerants F1-F6 were previously collected in separate collection tanks RC during a collective recovery operation, as will be described in more detail hereafter.

This document presents the example of six fluorinated fluids F1-F6, however it goes without saying that the number of fluorinated fluids F1-F6 collected may be different, in particular, greater than six.

Each fluorinated fluid F1-F6 consists of a pure chemical component Cx or a mixture of chemical components Cx.

Preferably, each chemical component Cx is a chemical molecule of the hydrofluorocarbon HFC, hydrochlorofluorocarbon HCFC, hydrofluoroolefin HFO or hydrochlorofluoroolefin HCFO type. For the sake of brevity, in the remainder of this document, the hydrofluoroolefin components, designated HFO/HCFO, refer to both hydrofluoroolefins HFO and hydrochlorofluoroolefins HCFO. Further preferably, at least one of the chemical mixtures M1-M4 comprises at least one hydrofluoroolefin HFO/HCFO molecule.

In this example, the HFC and HCFC components are preferably chosen from the following list of components: R-134a, R-125, R-32, R227ea, R-143a and R22. Similarly, in this example, the HFO/HCFO components are preferably chosen from the following list of components: R-1234yf, R1234ze, R1233zd.

Figure 1:
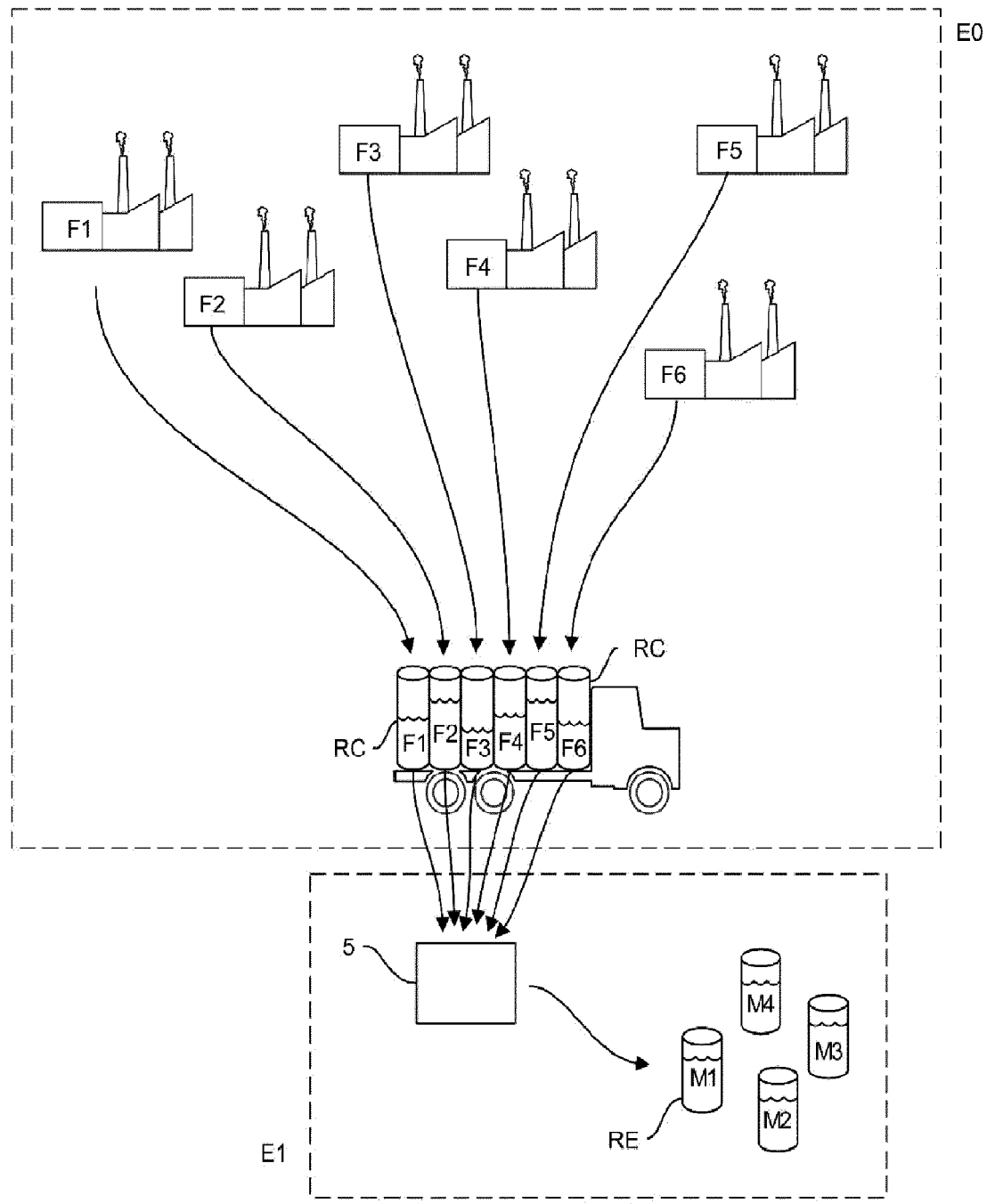
FIG. 1 is a schematic representation of a preliminary step of collecting several fluorinated fluids having different compositions and of distributing each fluorinated fluid collected into several mixtures.

In this example, still with reference to [FIG. 1], once collected, each fluorinated fluid F1-F6 is configured to be analyzed by a sorting system, in the form of an electronic device 5 and comprising sensors of different types to classify the fluorinated fluids F1-F6 according to its properties and nature.

In this example, all the fluorinated refrigerants F1-F6 are classified into four groups, each corresponding to a list of components among the components mentioned above. All the fluorinated fluids F1-F6 of a same group are configured to be mixed, so as to form one or more mixtures of fluorinated fluids F1-F6, in this example four chemical mixtures M1-M4.

In this example, the four chemical mixtures M1-M4 preferably comprise the components listed in the following table 1, among the chemical components targeted by the separation system S according to the invention (it goes without saying that each fluorinated fluid F1-F6 may comprise certain chemical components not targeted by the invention, such as for example R12, R152a, R290, R600, R600a, R601a, RE170):

TABLE 1

| Mixture | Authorized components | Components authorized in limited quantity, i.e. preferably less than 20% | Unauthorized components |
|---|---|---|---|
| M1 | R32, R125, R134a, R1234yf, R1234zc | / | R143 a, R227ea, R22 |
| M2 | R125, R143a, R134a | R1234ze, R227ea | R32, R1234yf, R22 |
| M3 | R22 | R32, R125, R143a, R134a, R1234yf, R1234ze, R227ea | / |
| M4 | R227ea | R32, R125, R143a, R134a, R22 | R1234yf, R1234ze |

In this example, each chemical mixture M1-M4 thus results from a single fluorinated fluid F1-F6 collected or from the mixture of several fluorinated fluids F1-F6 collected. Each chemical mixture M1-M4 will preferably be treated independently by the separation system S according to the invention. In the prior art, each fluorinated fluid F1-F6 had to be treated completely independently, and the recovery and separation of components was individual and not collective.

Figure 2:
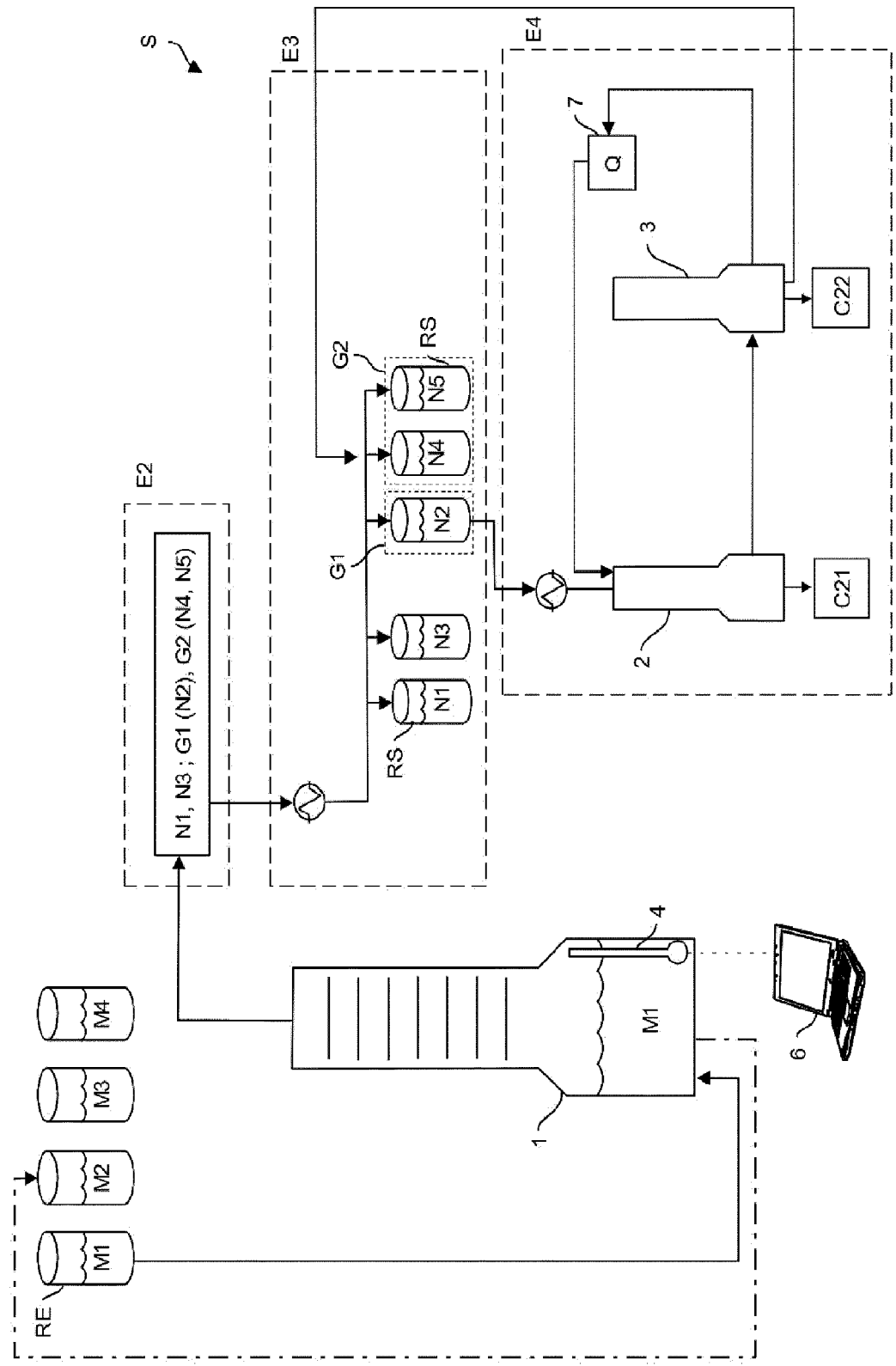
FIG. 2 is a schematic representation of the separation system according to one embodiment of the invention.
Figure 3:
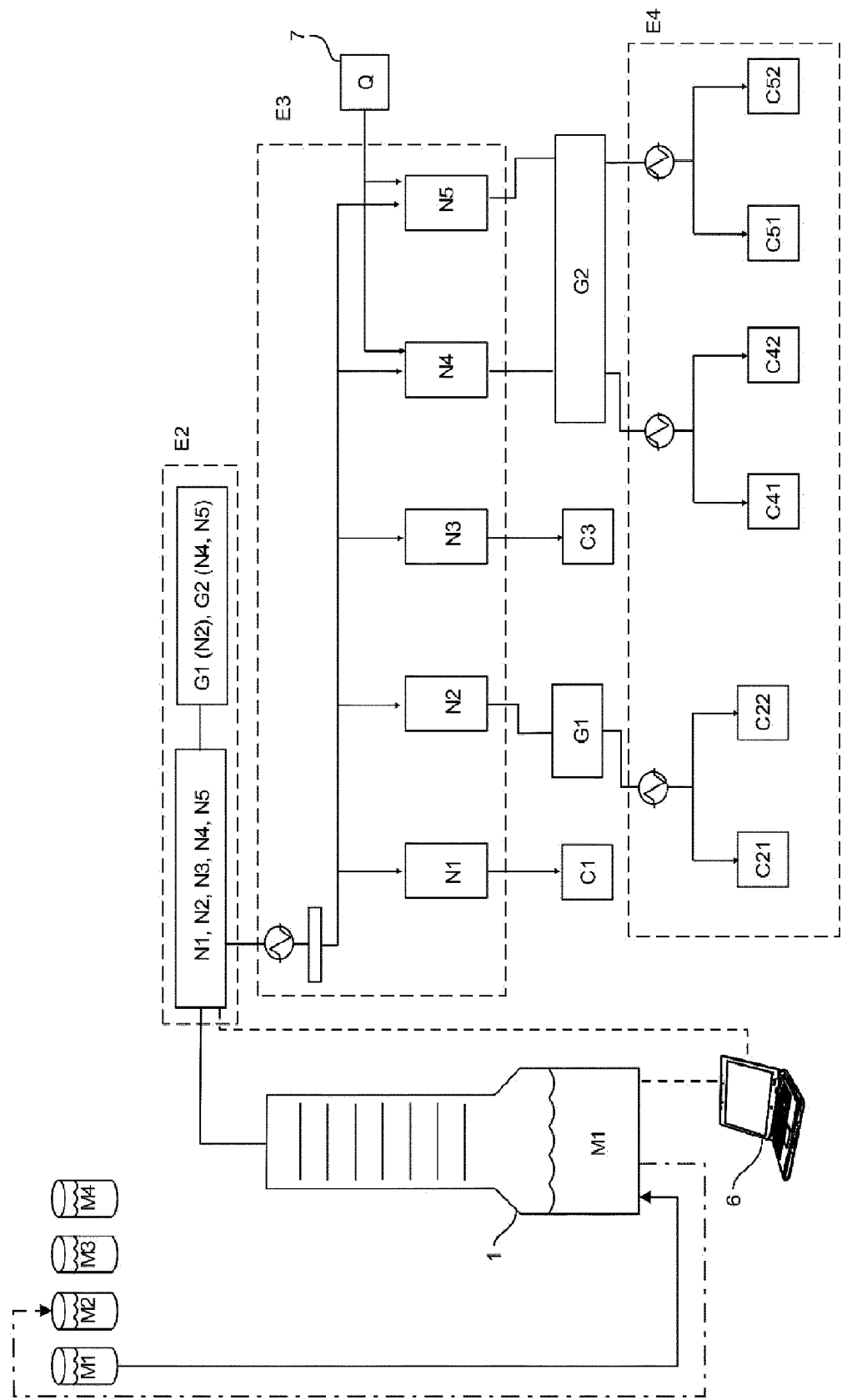
FIG. 3 is a schematic representation of the steps of a separation process according to the invention.

According to the invention, with reference to FIGS. 2 and 3, each chemical mixture M1-M4 is configured to be separated in a primary distillation into a plurality of sub-mixtures N1-N5, each sub-mixture N1-N5 comprises either a pure chemical component Cx, or a combination of chemical components Cx. Such an operation will be described in more detail later in this document.

In this example, as shown in [FIG. 3], the chemical mixture MI comprises five sub-mixtures N1-N5, each sub-mixture N1-N5 comprises the following chemical components Cx or combinations of chemical components Cx:
- the sub-mixture N1 is a simple sub-mixture comprising a single pure chemical component CI;
- the sub-mixture N2 is a complex sub-mixture comprising an azeotropic composition of two chemical components C21, C22;
- the sub-mixture N3 is a simple sub-mixture comprising a single pure chemical component C3;
- the sub-mixture N4 is a complex sub-mixture comprising an azeotropic composition of two chemical components C41, C42; and
- the sub-mixture N5 is a complex sub-mixture comprising an azeotropic composition of two chemical components C51, C52.

For the sake of simplicity and brevity, each complex sub-mixture N2, N4, N5 comprises in this document two chemical components C21, C22, C41, C42, C51, C52. However, it goes without saying that each complex sub-mixture may comprise a different number of chemical components, in particular three chemical components.

In one preferred embodiment, each sub-mixture N2, N4, N5 comprising a combination of chemical components Cx is azeotropic or tight.

The separation process according to the invention is carried out by means of a separation system S according to the invention.

With reference to [FIG. 2], the separation system S according to the invention comprises a main column 1 for recovering a chemical mixture M1-M4 of fluorinated fluids F1-F6, configured to implement a simple distillation (also called primary distillation), and an advanced unit of two auxiliary columns 2, 3 for extraction, configured to implement an advanced distillation (also called secondary distillation). In the separation system according to the invention, the same two auxiliary columns 2, 3 of the advanced unit allow both an extractive distillation by means of an entrainer and a distillation by pressure swing. The advanced unit thus comprises a first auxiliary column 2 and a second auxiliary column 3.

The main column 1 is configured to receive one of the chemical mixtures M1-M4 of fluorinated fluids F1-F6 previously classified. The main column 1 is connected by means of appropriate piping to a plurality of storage tanks RS, each configured to receive one of the sub-mixtures N1-N5 of the chemical mixture M1-M4, after the simple distillation operation.

The main column 1 allows direct extraction of each pure component C1, C3, after simple distillation and separation of the sub-mixtures N1-N5, in particular of the simple sub-mixtures N1, N3, as shown in [FIG. 3].

With reference to [FIG. 2], the first auxiliary column 2 of the advanced unit is connected by suitable piping to one of the storage tanks RS of one of the complex sub-mixtures N2, N4, N5 and is configured to successively receive each sub-mixture N2, N4, N5, as will also be described in more detail hereafter.

The second auxiliary column 3 of the advanced unit is connected directly to the first auxiliary column 2, comprising one of the complex sub-mixtures N2, N4, N5 comprising a combination of chemical components C21, C22, C41, C42, C51, C52.

The separation system S further comprises an identification device 4 of the plurality of sub-mixtures N1-N5 from all the chemical components Cx present in the chemical mixture M1-M4. The identification device 4 is, for example, in the form of a qualitative and quantitative analysis system (e.g. a chromatographic analysis system) of the mixtures M1-M4 and the sub-mixtures N2, N4, N5. Thus, the identification device 4 is configured to detect each chemical component Cx present in the chemical mixture M1-M4 and in each sub-mixture N2-N4-N5.

According to one embodiment of the invention, the separation system S also comprises an external electronic calculator 6, for example a computer, electrically connected to the identification device 4. The electronic calculator 6 is configured to determine, for each identified sub-mixture N1-N5, whether it is a simple sub-mixture N1-N5 comprising a single pure chemical component Cx or a complex sub-mixture N1-N5 comprising a combination of chemical components Cx. The electronic calculator 6 is further configured to determine, for each complex sub-mixture N1-N5, an advanced distillation method to allow separation of the chemical components Cx from the azeotropic composition of each. The advanced distillation method is determined according to the invention from a pressure swing distillation method and a solvent extraction distillation method. These distillation methods are known to those skilled in the art and will not be described in more detail in this document. In other words, the electronic control unit 6 makes it possible to coordinate the successive treatment of the sub-mixtures N1-N5 in order to separate the components Cx.

Preferably, to determine the appropriate advanced distillation method for each complex sub-mixture N1-N5, the electronic calculator 6 is configured to identify in a database (see table 3) each of the combinations of chemical components as well as the advanced distillation method associated with each. In other words, such a database comprises all the pure chemical components Cx and combinations of chemical components Cx potentially present in a fluorinated fluid F1-F6, as well as the advanced distillation method that makes it possible to separate each combination of chemical components Cx. The electronic calculator 6 is further configured to classify each complex sub-mixture N1-N5 by associating each with a first group G1 comprising the sub-mixtures N1-N5 (in this example only the sub-mixture N2) which have to be distilled by the advanced pressure swing method or with a second group G2 comprising the sub-mixtures N1-N5 (in this example the sub-mixtures N4 and N5) which have to be distilled by the advanced extraction method.

The separation system S further comprises a solvent tank 7 configured to supply the first auxiliary column 2 when the latter is configured to undergo an extraction distillation method by means of a solvent. The solvent tank 7 comprises a solvent Q (also known as an entrainer) chosen from ketones, halogenated alkanes (C4 to C7), alkanes (C4 to C7) and ethers. Preferably, the solvent Q is selected from the following list: n-pentane, dichloromethane, methyl isobutyl ketone (MIBK), methyl ethyl ketone (MEK), heptanone, pentanone, cyclohexanone and dimethylether. Preferably still, the solvent Q used is methyl isobutyl ketone since it has advantages in terms of selectivity power and recovery.

A process for separating the chemical components Cx present in the chemical mixture M1-M4 of fluorinated fluids F1-F6 according to the invention, with reference to FIGS. 1 to 3, will henceforth be described. The separation process according to the invention aims to individually separate the plurality of chemical components Cx present in a chemical mixture M1-M4 as described previously. Each mixture M1-M4 is successively introduced into the separation system S.

Preferably, the separation process according to the invention allows the separation of all the chemical components Cx of a chemical mixture M1-M4 in which each chemical component Cx may be either a hydrofluorocarbon HFC, a hydrochlorofluorocarbon HCFC, or a hydrofluoroolefin HFO/HCFO.

With reference to [FIG. 1], the separation process comprises a preliminary step of collecting E0 a plurality of fluorinated fluids F1-F6. In this step, for example, an operator moves to different locations to collect the fluorinated fluids F1-F6 from a plurality of different thermodynamic devices. For example, each fluorinated fluid F1-F6 is collected during an operation of air conditioning system maintenance, in agriculture or during aerosol purges, for example.

In this preliminary step E0, the operator recovers each fluorinated fluid F1-F6 in a plurality of different collection tanks RC.

Each fluorinated fluid F1-F6 is then analyzed in a step E1, by an electronic device 5, in order to determine which chemical components Cx are present in each fluorinated fluid F1-F6. In this first step EI, the fluorinated refrigerants F1-F6 are classified, in this example, into four groups and then mixed, so as to form four chemical mixtures M1-M4. Each chemical mixture M1-M4 represents a set of predetermined chemical components Cx. According to the chemical components Cx present in all the fluorinated fluids F1-F6, it goes without saying that each chemical mixture M1-M4 may comprise a mixture of several fluorinated fluids F1-F6, a single fluorinated fluid F1-F6 or no fluorinated fluid F1-F6. The chemical mixtures M1-M4 advantageously allow simultaneous overall treatment of several fluorinated fluids F1-F6 and not on a case-by-case treatment basis.

All the chemical mixtures M1-M4 are then stored in independent containers RE. Each chemical mixture M1-M4 will be treated independently. Subsequently, the separation process will be described for the separation of the chemical components Cx present in the chemical mixture M1.

With reference to [FIG. 3], the chemical mixture M1 is transferred to the main column 1 of the separation system S.

The composition of the chemical mixture M1 is analyzed via the identification device 4 connected to the electronic control unit 6. The process then comprises a step of identification E2 in the chemical mixture MI of a plurality of sub-mixtures N1-N5 by the electronic calculator 6. Each sub-mixture N1-N5 comprises a single chemical component Cx or a combination of chemical components Cx. As described previously, in this example shown in [FIG. 3], five sub-mixtures N1-N5 are identified and comprise the components listed in the following table 2.

TABLE 2

| Mixture | Sub-mixtures identified | Pure component or combination of components |
|---|---|---|
| M1 | N1 | C1 |
|  | N2 | C21, C22 |
|  | N3 | C3 |
|  | N4 | C41, C42 |
|  | N5 | C51, C52 |

The determination of the sub-mixtures N1-N5 is advantageous since it makes it possible to pre-determine whether the sub-mixture N1-N5 requires advanced distillation and which advanced distillation method will be required to separate all the chemical components.

The number and the composition of the sub-mixtures N1-N5 are only given here by way of example, however it goes without saying that the number of sub-mixtures N1-N5 in each chemical mixture M1-M4 may be different.

The identified complex sub-mixtures N1-N5 are also classified so as to be separated into a first group G1 and a second group G2. According to the invention, the first group G1 comprises all the sub-mixtures (in this example only the sub-mixture N2) comprising a combination of chemical components Cx that can be separated by an advanced pressure swing distillation method. The second group G2 comprises the set of sub-mixtures (in this example the sub-mixtures N4, N5) comprising a combination of chemical components Cx which can be separated by an advanced extraction distillation method.

Such a classification is preferably carried out by the electronic calculator 6, based on the database. In this example, the electronic calculator 6 makes it possible to establish the identifications and classifications listed in table 3 below using its database:

TABLE 3

| Sub-mixtures | Components | Group | Distillation method |
|---|---|---|---|
| N1 | C1 | / | / |
| N2 | C21, C22 | G1 | Distillation by pressure swing |
| N3 | C3 | / | / |
| N4 | C41, C42 | G2 | Distillation by extraction |
| N5 | C51, C52 | G2 | Distillation by extraction |

Still with reference to [FIG. 3], the separation process next comprises a step of primary distillation E3, by the main distillation column 1, of the chemical mixture MI, so as to separate each identified sub-mixture N1-N5 in an independent storage tank RS.

The process then comprises a secondary distillation step E4 of each complex sub-mixture N2, N4, N5 by means of the advanced unit of two auxiliary columns 2, 3. More precisely, this step allows the advanced distillation of each complex sub-mixture N1-N5 of the first group G1, in this example only the sub-mixture N2, and each complex sub-mixture N1-N5 of the second group G2, in this example the sub-mixtures N4 and N5. Each complex sub-mixture N2, N4, N5 is distilled independently, also all the complex sub-mixtures N2, N4, N5 are successively subjected to a secondary distillation by the advanced unit of two auxiliary columns 2, 3.

In this secondary distillation step E4, the complex sub-mixture N2 of the first group G1 is distilled by the pressure swing method, so as to separate the chemical components C21, C22 from the complex sub-mixture N2 of the first group G1.

In this step, as is known, the first auxiliary column 2 is set to a first pressure and the second auxiliary column 3 is set to a second pressure, strictly different from the first pressure to allow separation of different components C21, C22.

In this secondary distillation step E4, each complex sub-mixture N4, N5 of the second group G2 is distilled by the extraction distillation method, using the same solvent Q, so as to separate the chemical components C41, C42, C51, C52 from each complex sub-mixture N4, N5 of the second group G2.

When the complex sub-mixture N4, N5 has to be separated by the extraction distillation method, the solvent Q is then injected into the first auxiliary column 2. The solvent Q next passes into the second auxiliary column 3 and is then recovered in the solvent tank 7 so as to be recycled for use in a subsequent extraction distillation. Indeed, in one preferred embodiment, all the complex sub-mixtures N4, N5 of the second group G2 are distilled using a single solvent Q. Preferably, the solvent Q is one of the following solvents: n-pentane, dichloromethane, methyl isobutyl ketone (MIBK), methyl ethyl ketone (MEK), heptanone, pentanone, cyclohexanone and dimethylether. Preferably still, the solvent Q used is methyl isobutyl ketone. Preferably, the solvent tank 7 is connected directly to the first extraction auxiliary column 2, so as to supply it with solvent Q. Similarly, the solvent tank 7 is supplied in return by the solvent Q, recovered directly from the second auxiliary extraction column 3 (as shown in [FIG. 2]).

Such an extraction distillation method is advantageous given that a single Q solvent is used, which reduces material and logistics costs. Thus, any type of mixture M1-M4 can be treated dynamically, the distillation steps being performed according to the dynamically identified sub-mixtures N1-N5.

At the end of the separation process according to the invention, each chemical component Cx present in the chemical mixture M1 of fluorinated fluids F1-F6 is separated from the other chemical components Cx. The other chemical mixtures M2-M4 are then successively introduced into the main column 1 and steps E2 to E4 are repeated in order to individually separate each component Cx from each chemical mixture M2-M4.

Such a process according to the invention advantageously makes it possible to efficiently separate chemical components from a mixture of several fluorinated fluids, without requiring the case-by-case treatment of each fluorinated fluid which would require adaptation of the separation system S to each refrigerant.

Thanks to the separation process according to the invention, the chemical components of several fluorinated fluids from different thermodynamic devices can be separated by means of a single separation system, which represents a significant time saving.

In addition, during the separation process, the same separation system can be used successively for different chemical mixtures of fluorinated fluids, which makes it possible to significantly limit costs, because the same unit of two extraction columns can be used regardless of the advanced distillation method required to separate the different components of the chemical mixture.

The invention also relates to a method for recycling each chemical component. For this purpose, following the different steps of the process, the recycling method comprises a step of recycling each separate chemical component for later reuse.

The invention claimed is:

1. Process for separating a plurality of chemical components from a chemical mixture, the chemical mixture comprising a plurality of fluorinated fluids, each fluorinated fluid comprising at least one fluorinated chemical component, the process comprising:
   a step of identification in the chemical mixture of at least two sub-mixtures, each sub-mixture being a simple sub-mixture comprising a single chemical component or a complex sub-mixture comprising a combination of chemical components, each complex sub-mixture being associated either with a first secondary distillation group by a pressure swing distillation method, or with a second secondary distillation group by an extraction distillation method,
   a primary distillation step, by means of a simple main distillation column, so as to separate each identified sub-mixture,
   a secondary distillation step, by means of a same advanced unit of two auxiliary extraction columns, of each complex sub-mixture of the first group and of the second group, the complex sub-mixtures of the first group being separated by the pressure swing distillation method and the complex sub-mixtures of the second group being separated via a predetermined solvent, by the extraction distillation method, by the same two auxiliary columns.

2. Separation process according to claim 1, wherein each complex sub-mixture is azeotropic or tight.

3. Separation process according to claim 1, wherein the solvent is selected from the following solvents: n-pentane, dichloromethane, methyl isobutyl ketone, methyl ethyl ketone, heptanone, pentanone, cyclohexanone and dimethylether.

4. Separation process according to claim 1, wherein at least one of the chemical components of at least one sub-mixture is a hydrofluoroolefin HFO, a hydrochlorofluoroolefin HCFO, a hydrofluorocarbon HFC or a hydrochlorofluorocarbon HCFC.

5. Separation process according to claim 1, wherein the identification step is performed from a database associating the sub-mixtures with a secondary pressure swing distillation method or a secondary extraction distillation method.

6. Separation process according to claim 1, comprising a preliminary step of collecting a plurality of fluorinated fluids comprising different chemical components and mixing a plurality of fluorinated fluids from the fluorinated fluids collected, so as to form at least one chemical mixture of fluorinated fluids.

7. Method for recycling the plurality of chemical components of a chemical mixture of fluorinated fluids comprising the steps of the separation process according to claim 1 and a step of independent recycling each of the plurality of chemical components for use in refrigeration.

8. Separation system for implementing the method according to claim 1, the separation system comprising:
   a simple main distillation column, configured to receive the chemical mixture of fluorinated fluids and implement a primary distillation, so as to separate the chemical mixture into at least two sub-mixtures,
   an electronic calculator configured to:
      identify in the chemical mixture the different sub-mixtures, each sub-mixture being a simple sub-mixture comprising a single chemical component or a complex sub-mixture comprising a combination of chemical components,
      associate each complex sub-mixture either with a first secondary distillation group by a pressure swing method, or with a second secondary distillation group by an extraction distillation method,
      an advanced unit comprising two auxiliary extraction columns, configured to implement a secondary distillation and to allow both a distillation by extraction by means of an entrainer and a distillation by pressure swing, so as to separate all the chemical components from each sub-mixture.

9. Separation system according to claim 8, wherein the advanced unit consists of two auxiliary columns, configured to enable the implementation either of an advanced distillation by extraction or an advanced distillation by pressure swing.

10. Separation system according to claim 8, comprising a solvent tank configured to supply one of the two auxiliary columns when the latter receives a complex sub-mixture of the second group.

\* \* \* \* \*